(12) United States Patent
Ahearn

(10) Patent No.: US 8,360,058 B2
(45) Date of Patent: Jan. 29, 2013

(54) NITROUS OXIDE ANESTHETIC ADMINISTRATION SYSTEM

(76) Inventor: David J. Ahearn, Little Compton, RI (US)

( * ) Notice: Subject to any disclaimer, the term of this patent is extended or adjusted under 35 U.S.C. 154(b) by 648 days.

(21) Appl. No.: 12/567,729

(22) Filed: Sep. 25, 2009

(65) Prior Publication Data

US 2010/0071694 A1    Mar. 25, 2010

Related U.S. Application Data

(60) Provisional application No. 61/100,149, filed on Sep. 25, 2008.

(51) Int. Cl.
*A61M 11/00* (2006.01)

(52) U.S. Cl. .............. 128/203.28; 5/623; 248/118.1; 248/424

(58) Field of Classification Search ........... 128/205.12, 128/205.28, 205.29, 203.28, 846–848; 5/623, 5/624; 248/118.1, 121, 122.1, 424
See application file for complete search history.

(56) References Cited

U.S. PATENT DOCUMENTS

| | | | |
|---|---|---|---|
| 340,778 A | 4/1886 | Gilbert | |
| 2,225,201 A | 12/1940 | Anderson | |
| 3,176,687 A | 4/1965 | Barach | |
| 3,198,574 A | 8/1965 | Sadayasu Ota et al. | |
| 3,259,430 A | 7/1966 | Beach | |
| 3,262,735 A | 7/1966 | Thompson | |
| 3,556,097 A * | 1/1971 | Wallace | 128/202.23 |
| 3,747,600 A * | 7/1973 | Andersson | 128/203.25 |
| 3,761,968 A | 10/1973 | Besler | |
| 3,771,226 A * | 11/1973 | Lieb et al. | 433/33 |
| 3,785,377 A | 1/1974 | Jorgensen | |
| 3,802,736 A | 4/1974 | Valeska et al. | |
| 4,109,958 A | 8/1978 | Grupelli | |
| 4,114,946 A | 9/1978 | Hoffmeister et al. | |
| 4,188,946 A | 2/1980 | Watson et al. | |
| 4,310,307 A | 1/1982 | Bellisario | |
| 4,360,018 A * | 11/1982 | Choksi | 128/205.12 |
| 4,391,588 A | 7/1983 | Matsui | |
| 4,427,382 A * | 1/1984 | Hoffmeister et al. | 433/79 |
| 4,538,605 A | 9/1985 | Gedeon et al. | |
| 4,934,933 A | 6/1990 | Fuchs | |
| 5,601,331 A * | 2/1997 | Austin et al. | 297/170 |
| 5,676,133 A | 10/1997 | Hickle et al. | |
| 6,234,172 B1 | 5/2001 | Ausbourne et al. | |
| 6,406,294 B1 * | 6/2002 | Bell | 433/33 |
| 6,412,801 B1 | 7/2002 | Izuchukwu et al. | |

(Continued)

FOREIGN PATENT DOCUMENTS

EP    0584439 A1    2/1994

*Primary Examiner* — Steven Douglas
(74) *Attorney, Agent, or Firm* — Barlow, Josephs & Holmes, Ltd.

(57) ABSTRACT

The present invention is a system for administering nitrous oxide. The system includes an adjustable post mechanism attached to a dental chair. A mounting surface structure includes a top surface and a bottom surface. The bottom surface of the mounting surface structure attached to a top end of the adjustable post mechanism. A fluid control system for controlling the flow of nitrous oxide and oxygen is attached to the mounting surface structure. A nitrous oxide and oxygen supply, vacuum source, a breather bag, and a nasal delivery interface system are fluidly connected to the fluid control system and a patient. The breather bag is vertically mounted to a top surface of the mounting surface structure. In operation, the present invention provides a system for administering anesthesia/analgesia gas which provides convenient and direct access to a medical practitioner.

3 Claims, 19 Drawing Sheets

U.S. PATENT DOCUMENTS

| | | |
|---|---|---|
| 6,626,496 B2 | 9/2003 | Beach et al. |
| 6,948,493 B2 | 9/2005 | Dunlop |
| 7,195,219 B2 * | 3/2007 | Irwin et al. .................. 248/284.1 |
| 7,624,737 B2 * | 12/2009 | Klemm ......................... 128/848 |
| 2003/0145854 A1 | 8/2003 | Hickle |
| 2004/0094676 A1 * | 5/2004 | Cuomo ...................... 248/125.7 |
| 2007/0298368 A1 * | 12/2007 | Nam ................................ 433/25 |
| 2008/0122269 A1 | 5/2008 | Tatlock |

* cited by examiner

NITROUS OXIDE ANESTHETIC ADMINISTRATION SYSTEM

CROSS REFERENCE TO RELATED APPLICATION

This application is related to and claims priority from earlier filed provisional patent application Ser. No. 61/100,149, filed Sep. 25, 2008 and incorporated herein by reference.

BACKGROUND OF THE INVENTION

The present invention relates to a system for administering gas. More particularly, the present invention relates to a system for administering anesthesia/analgesia gas which provides convenient, direct access by a medical practitioner, a clear line of vision for the medical practitioner, and flexibility to accommodate the patient and medical professional's needs.

N2O analgesia has been used for over a century to successfully relax and sedate dental patients. Originally and until recently the application of these gages was virtually unrestricted and thus the supply system required was relatively unencumbered. With the advent of mandatory scavenge systems for nitrous delivery, these units became much more bulky and difficult to use in day to day practice and this utilized rate declined.

Typically, the compressed medical gages are delivered to the practitioner's facility in gas cylinders. These cylinders either connect to a central distribution system, serving multiple operating rooms, or they are portable and are mounted on rolling carts which serve one operating room and patient. These cylinders are connected via hoses or piping to a regulating system which controls delivery pressure, flow rate and blended ratio. There are monitors, gages and other devices to provide information to the practitioner regarding the delivery parameters. From the control device, gas flows via flexible hoses to a nasal delivery interface device. As shown in FIG. 1, vacuum scavenging of expelled gases flows from the nasal delivery interface device, via flexible tubing, into the centralized building vacuum utility system.

These essential components are incorporated into support systems. Systems commonly found in the art fall into three general categories: a) cart mounted tanks and controls, b) cart mounted controls and c) wall or stationary cabinet mounted controls.

Cart mounted tanks and control systems utilize an open or closed, wheeled cart. (FIGS. 4, 9). Portable O2 and N2O tanks are mounted on the cart. The control system and breather bag are usually mounted on a center pole attached to an open cart or supported by the shell of an enclosed cart. The patient supply tubing connects the cart outlet to the nasal delivery interface device. Referring to FIG. 2, the scavenging tubing connects the nasal delivery interface device via flexible tubing into the centralized building vacuum utility system.

As illustrated in FIGS. 1-2, current systems running from the control devices to the nasal delivery interface device use multi lumen hose systems which are long, heavy, complex and somewhat stiff. They pull on the patient's head and limit practitioner accessibility to the patient's mouth area. As a result they also limit the ability of the practitioner to reposition the patient's head.

Cart mounted control systems are similar to those above, except that the 02 and N20 are supplied from a central source via floor or wall gas outlets rather than from in situ tanks. Flexible hoses route the gases from the outlet to the control system. The control system and breather bag are mounted on a center pole attached to an open, wheeled cart. The patient supply tubing connects the cart outlet to the nasal delivery interface device. The scavenging tubing connects the nasal delivery interface device via flexible tubing into the centralized building vacuum utility system.

As illustrated in FIG. 3, wall and cabinet mounted systems have the O2 and N2O gas supplied via flexible or rigid tubing from a central source. This tubing is enclosed in the walls of the operatory with other centralized utilities. The control system and breather bag are mounted to the wall or cabinet unit. The mounting may be a flush mount, surface or articulated arm mount design. Long patient supply tubing connects the control systems to the nasal delivery interface device on the patient. Long scavenging system tubing connects the nasal delivery interface device into the centralized building vacuum utility system.

Also, wall mounted systems are typically separated from the patient chair by a work surface or passageway. Wall mount systems have long hose lengths between the control devices and the nasal delivery interface device. The longer the hose length, the longer the latency period between changing a control setting and the patient actually receiving that changed gaseous output. In addition, the hose position and length interferes with operator positioning. Tubing runs from the wall mounted, control system outlet to the nasal delivery interface device. This tubing crosses a passageway or work surface and blocks or encumbers which ever of these it traverses.

As illustrated in FIGS. 4-8, cart mounted systems can be located behind one of the practitioners or tucked under the back of the patient chair. In either case, visual monitoring of critical information in impeded. This is a dangerous situation because unknown changes occurring in the gaseous anesthetic system can be detrimental to the patient. Additionally, excess gas expelled into the operatory is harmful to the practitioners.

Also, carts located in the passageways, or workplace around the patient chair, cause inference as the practitioners move around the patient. Staff can trip over the carts and be injured and the flow of other technology and emergency access is impeded. As well as the cost of damaging an anesthetic system, rupturing any high pressure, 2000 psi, system can be very dangerous to all occupants of the operatory.

There are two main drawbacks of the systems describe above. First, current systems usually put the system controls out of direct reach of the medical professional when he/she is seated in normal treatment positions. This limitation is especially burdensome with wall mounted systems. This makes it difficult for the medical professional to accomplish anesthetic system adjustments without walking around or reaching around the patient. This awkward arrangement slows access and response to emergency situations. Second, current systems often put monitoring device displays and gauges out of direct view of the doctor and assistant.

Therefore, it would be particularly desirable to provide a system or method for anesthesia/analgesia gas delivery provides a nitrous oxide anesthetic administration system which provides convenient, direct access by a medical practitioner, a clear line of vision for the medical practitioner, and flexible to accommodate the patient and professional's needs. Currently, there is no known nitrous oxide anesthetic administration system in the prior art which provides these benefits.

BRIEF SUMMARY OF THE INVENTION

An embodiment of the present invention preserves the advantages of prior art nitrous oxide anesthetic administration systems or methods. In addition, it provides new advantages not found in currently available nitrous oxide anesthetic administration systems or methods and overcomes many disadvantages of such currently available nitrous oxide anesthetic administration systems or methods.

The present invention is a system for administering nitrous oxide which is preferably attached to a patient chair. The system generally includes: a mounting surface structure, a fluid control system attached to the mounting surface structure, a nasal delivery interface system connected to a patient and fluid control system, a nitrous oxide and oxygen supply connected to the fluid control system, a vacuum source for scavenging, a breather bag connected to the fluid control system, a mounting plate assembly to interface with patient or dental chairs, an adjustable post mechanism attached to the mounting plate assembly and the mounting surface structure, supply gas connectors and mixed gas output connectors attached to the fluid control system, and other hardware and tubing that is necessary to administer nitrous oxide in a health care environment, preferably a dentist's office.

The system includes an adjustable post mechanism attached to a patient or dental chair. The adjustable post mechanism is attached to a mounting plate assembly which is attached to a lower portion of a patient chair. The adjustable post mechanism is configured for height adjustment and pivotal adjustment to provide convenience of use to a practitioner.

The mounting surface structure includes a top surface and a bottom surface. The bottom surface of the mounting surface structure is attached to a top end of the adjustable post mechanism. The mounting surface structure positioned along a horizontal axis or approximately 180 degrees. The mounting surface structure attached to a breather bag a proximal end and a fluid control system at a distal end closest to a practitioner.

A fluid control system for controlling the flow of nitrous oxide and oxygen is attached to the mounting surface structure. The fluid control system including a fluid flow meter mounted on a top surface of the fluid control system. A display of the fluid flow meter positioned along a vertical axis at less than 90 degrees relative to the mounting surface structure to provide a better view to the practitioner. A nitrous oxide and oxygen supply fluidly connected to the fluid control system using fluid connectors fixedly attached to the bottom surface of said mounting surface structure.

A nasal delivery interface system fluidly connected to the fluid control system. The nasal delivery interface system including a single scavenging tube and a single nitrous oxide and oxygen tube fluidly connected to a single nasal delivery mask. The fluid control system including a mixed gas output connector fluidly connected to the single nitrous oxide and oxygen tube. A vacuum source fluidly connected to the single scavenging tube for scavenging excess gases and the fluid control system.

A breather bag is vertically mounted to a top surface of the mounting surface structure. The breather bag positioned along a vertical axis or about 90 degrees depending upwardly from the mounting surface structure. The breather bag mounted rearward or behind of the fluid control system to allow full view of fluid flow meter display. The breather bag fluidly connected to the control system by way of an elongated tubular structure attached to a front surface of the fluid flow meter.

In operation, the present invention provides a system for administering anesthesia/analgesia gas which provides convenient and direct access to a medical practitioner. The practitioner connects the nasal delivery interface system to the patient and to the fluid control system. After the nasal mask is attached to the patient, the nitrous oxide/oxygen gas is turned on and the gas enters a single tube fluidly connected with a nasal delivery mask. Throughout the administration of the gas, the system allows the practitioner a direct view and a close proximity to the upright breathing bag, fluid control system including display, patient, and all other parts of the nitrous oxide administration system which makes the administration of the gas much more efficient, safe, and less time consuming. Also, the mounting of the nitrous oxide anesthetic administration system to a patient's chair provides greater stability and convenience to a practitioner.

When the vacuum source is operational, any excess gases are scavenged from the patient through the nasal delivery mask, along a single scavenging tube, and returns back through the fluid control system. By only having two tubes, the patient and practitioner are given additional space and movement and reduce the possibility of entanglement.

It is therefore an object of the present invention to provide a method or system for a nitrous oxide anesthetic administration system which provides convenient access to nitrous oxide for a practitioner and patient.

It is a further object of the present invention to have direct access to the fluid control system and patient during administration of the nitrous oxide.

It is also an object of the present invention to provide a clear line of vision for the medical practitioner and flexibility to accommodate the patient and practitioner's needs.

Another object of the present invention is to eliminate the problems associated with current nitrous oxide delivery and scavenging systems.

Furthermore, another object of the present is to provide greater safety to patients and medical or dental persons during release of nitrous oxide in a medical or dental office.

Other objects, features and advantages of the invention shall become apparent as the description thereof proceeds when considered in connection with the accompanying illustrative drawings.

BRIEF DESCRIPTION OF THE DRAWINGS

The novel features which are characteristic of the nitrous oxide anesthetic administration systems and methods are set forth in the appended claims. However, the nitrous oxide anesthetic administration systems and methods, together with further embodiments and attendant advantages, will be best understood by reference to the following detailed description taken in connection with the accompanying drawings in which:

DETAILED DESCRIPTION OF PREFERRED EMBODIMENTS

Figure 1:
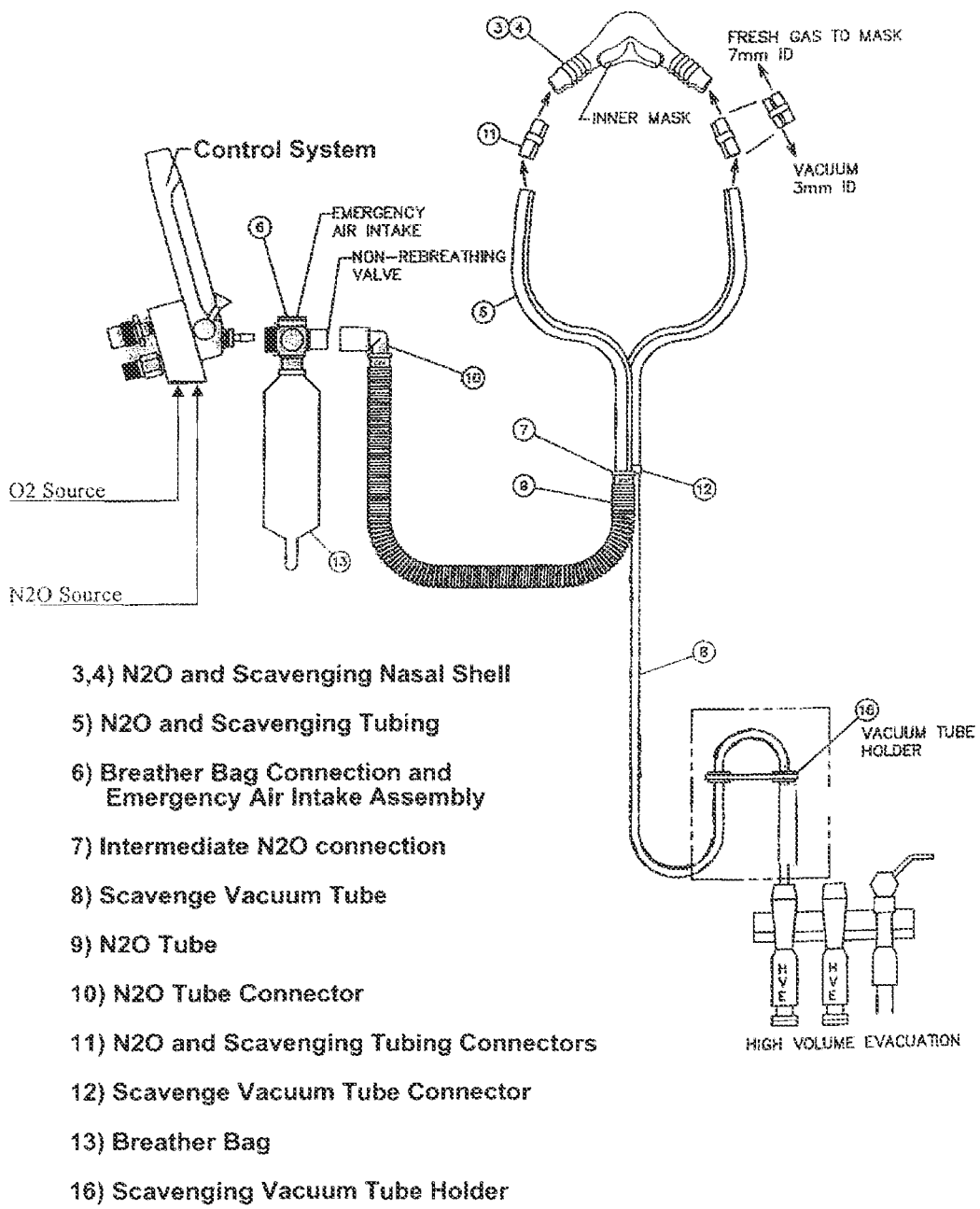
FIG. 1 is a prior art nitrous oxide anesthetic administration system.
Figure 2:
FIG. 2 is prior art nasal delivery interface device.
Figure 3:
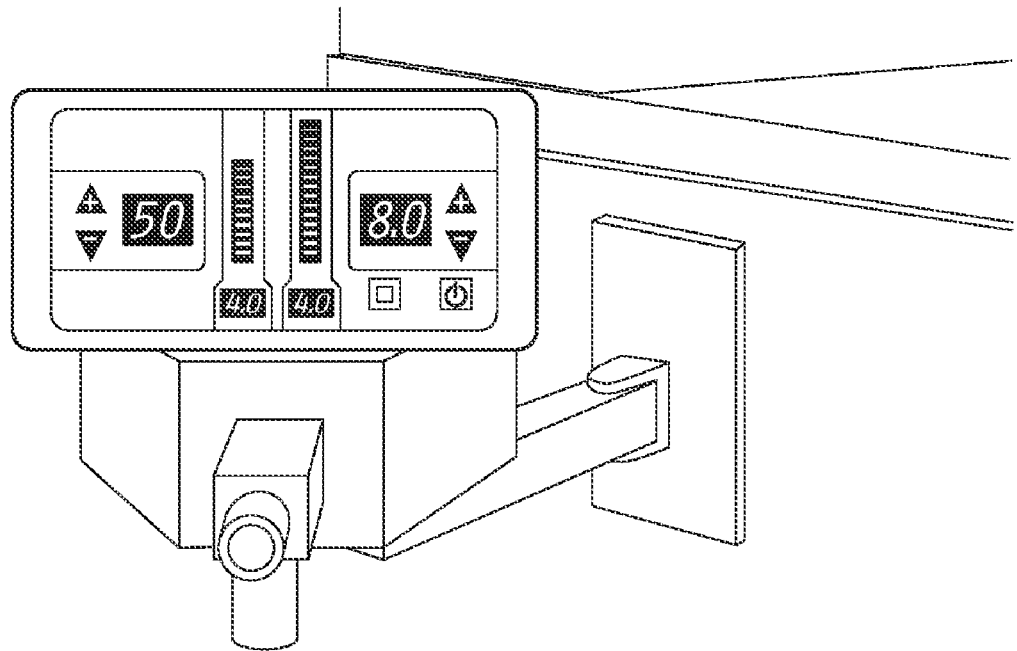
FIG. 3 is a prior art wall mounted nitrous oxide anesthetic administration system.
Figure 4:
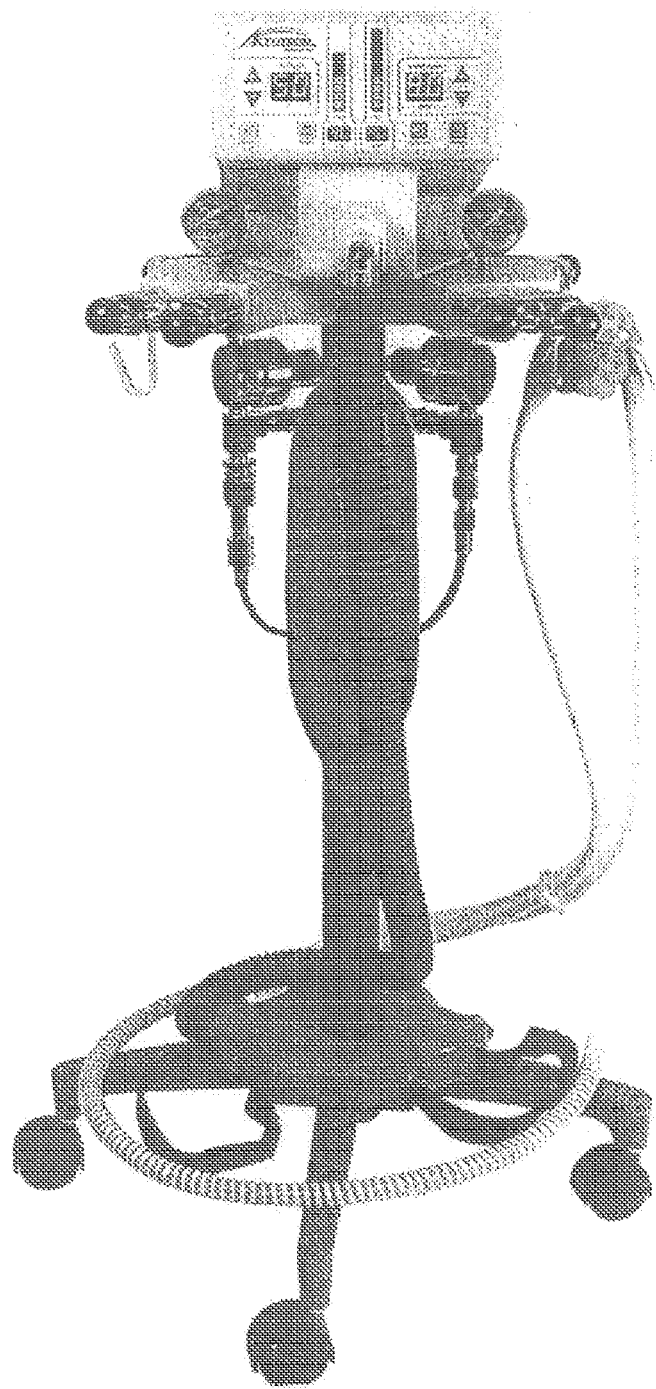
FIG. 4 is a prior art cart mounted nitrous oxide anesthetic administration system.
Figure 5:
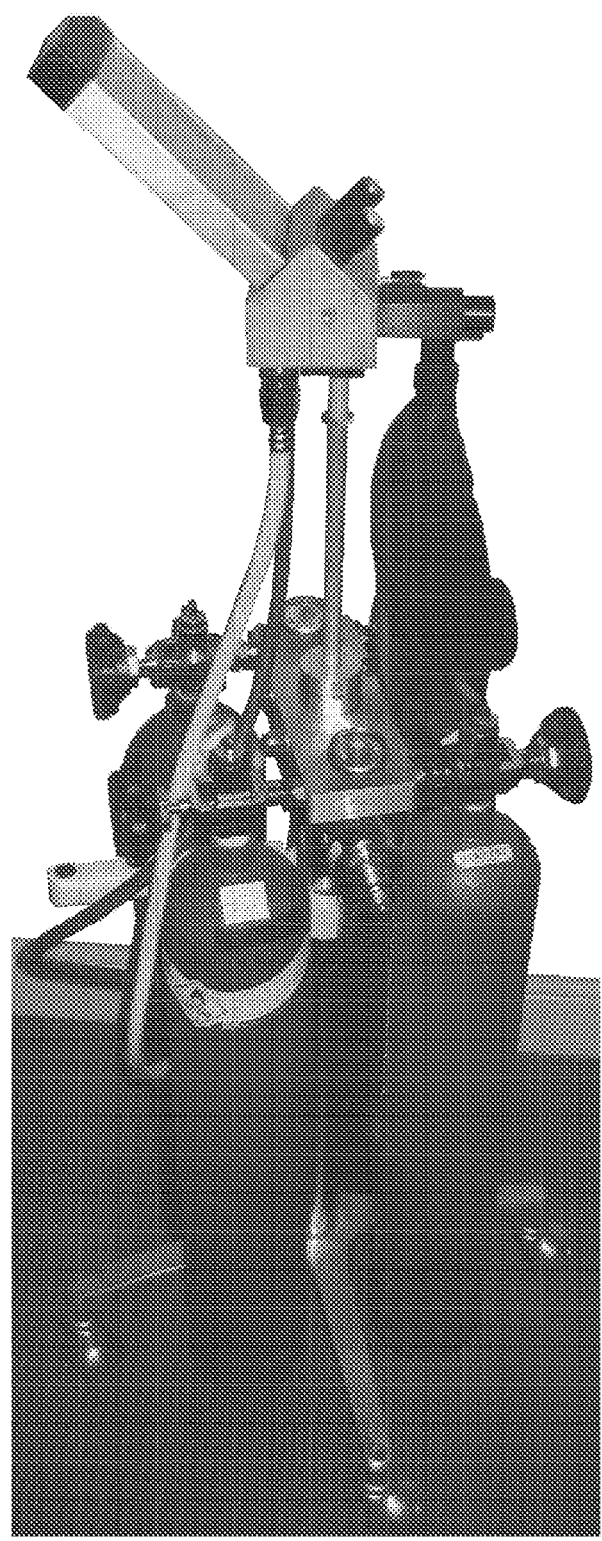
FIG. 5 is a prior art cart mounted nitrous oxide anesthetic administration system.
Figure 6:
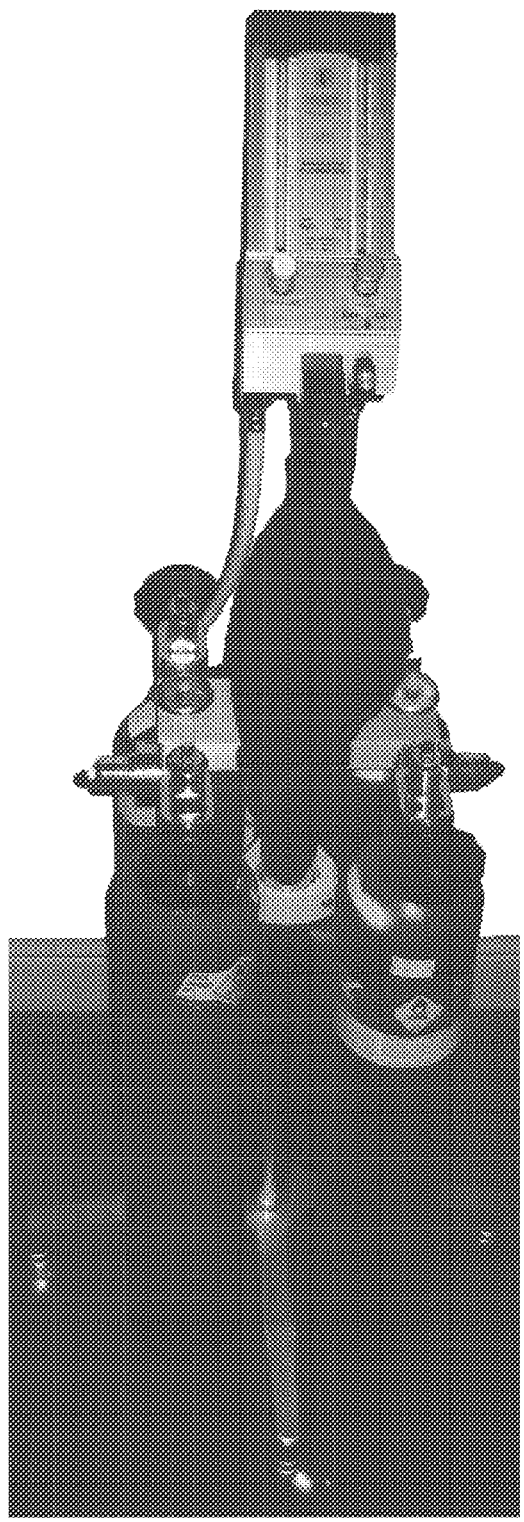
FIG. 6 is a prior art cart mounted nitrous oxide anesthetic administration system of FIG. 5.
Figure 7:
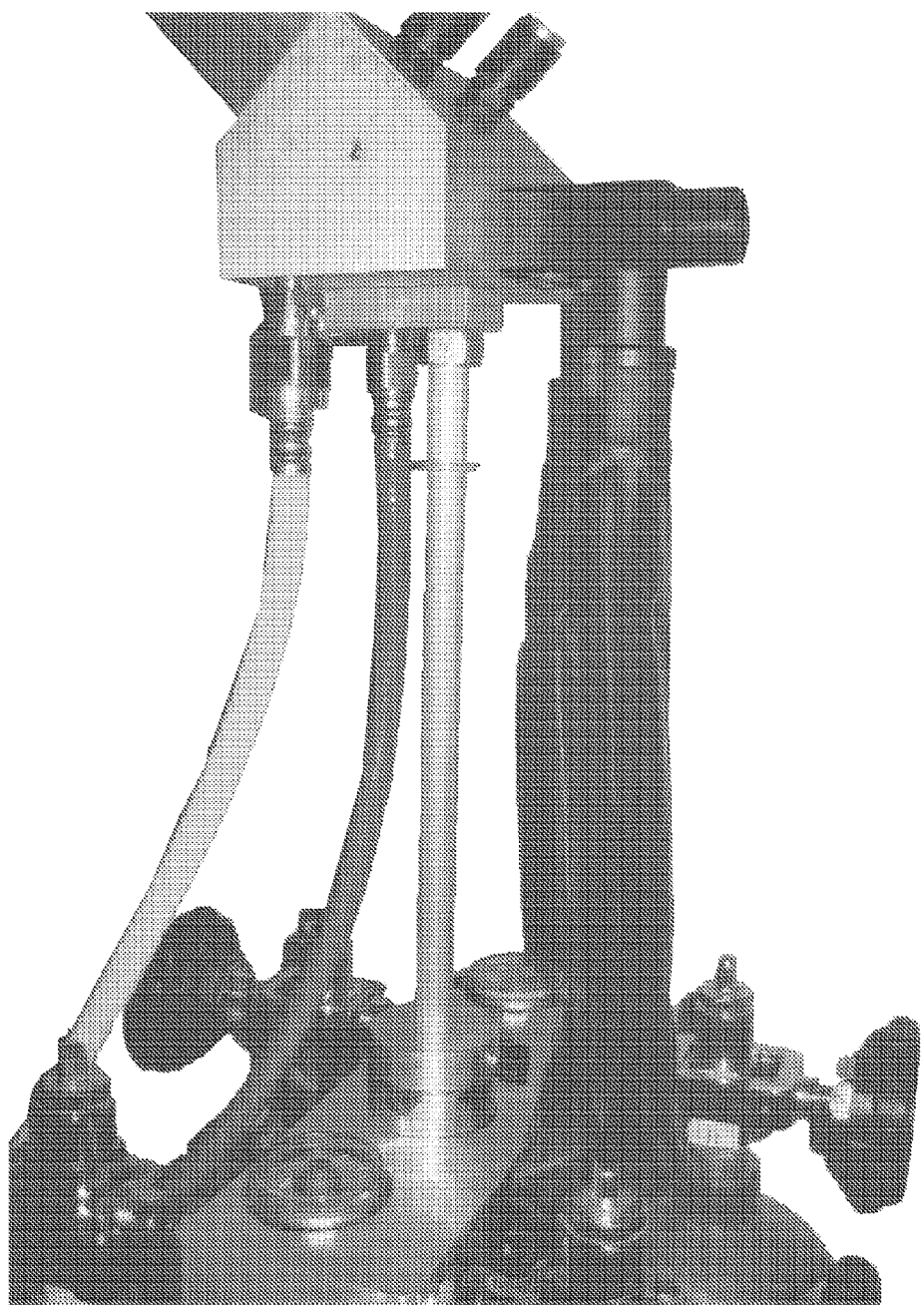
FIG. 7 is a prior art cart mounted nitrous oxide anesthetic administration system of FIG. 5.
Figure 8:
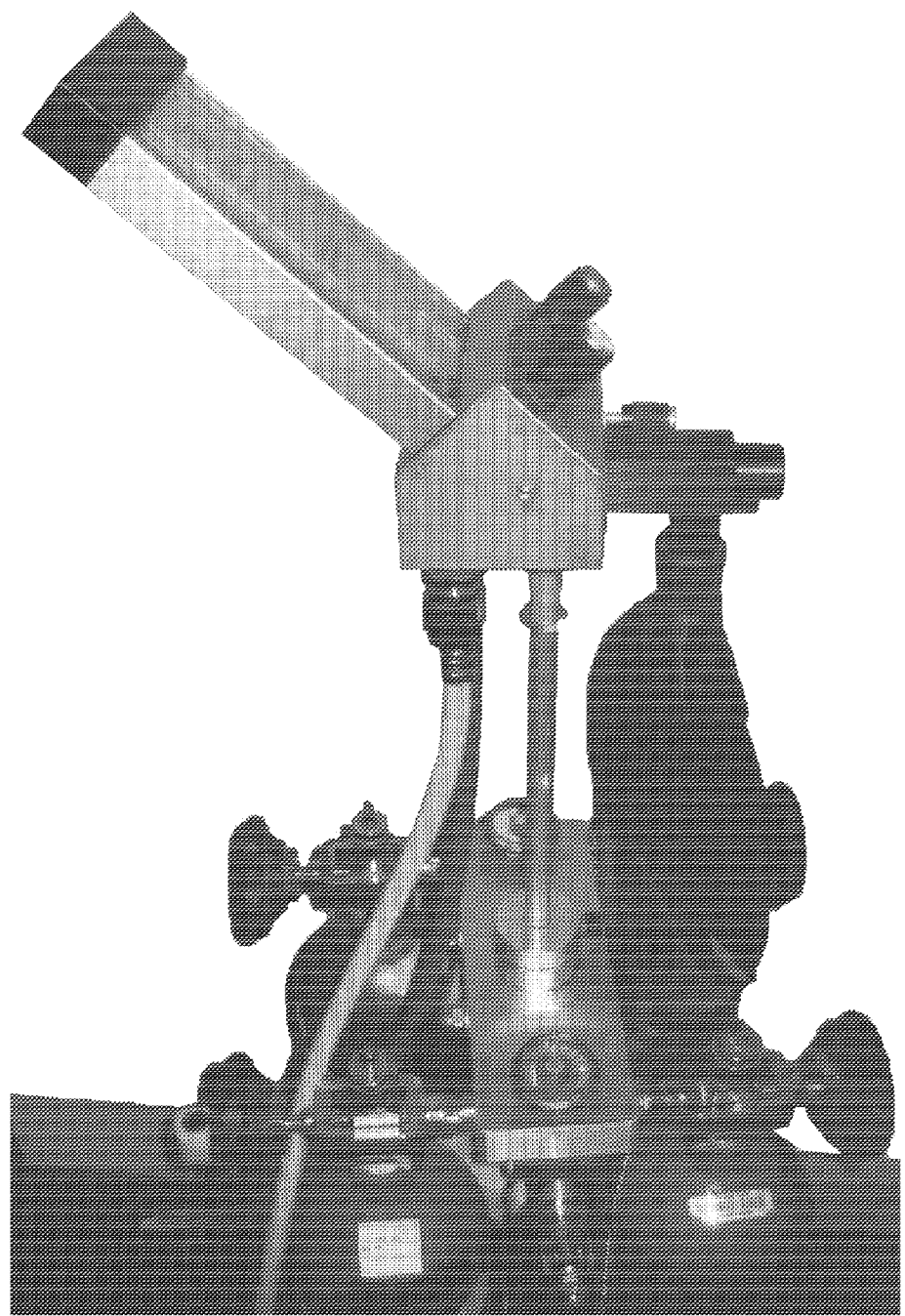
FIG. 8 is a prior art cart mounted nitrous oxide anesthetic administration system of FIG. 5.
Figure 9:
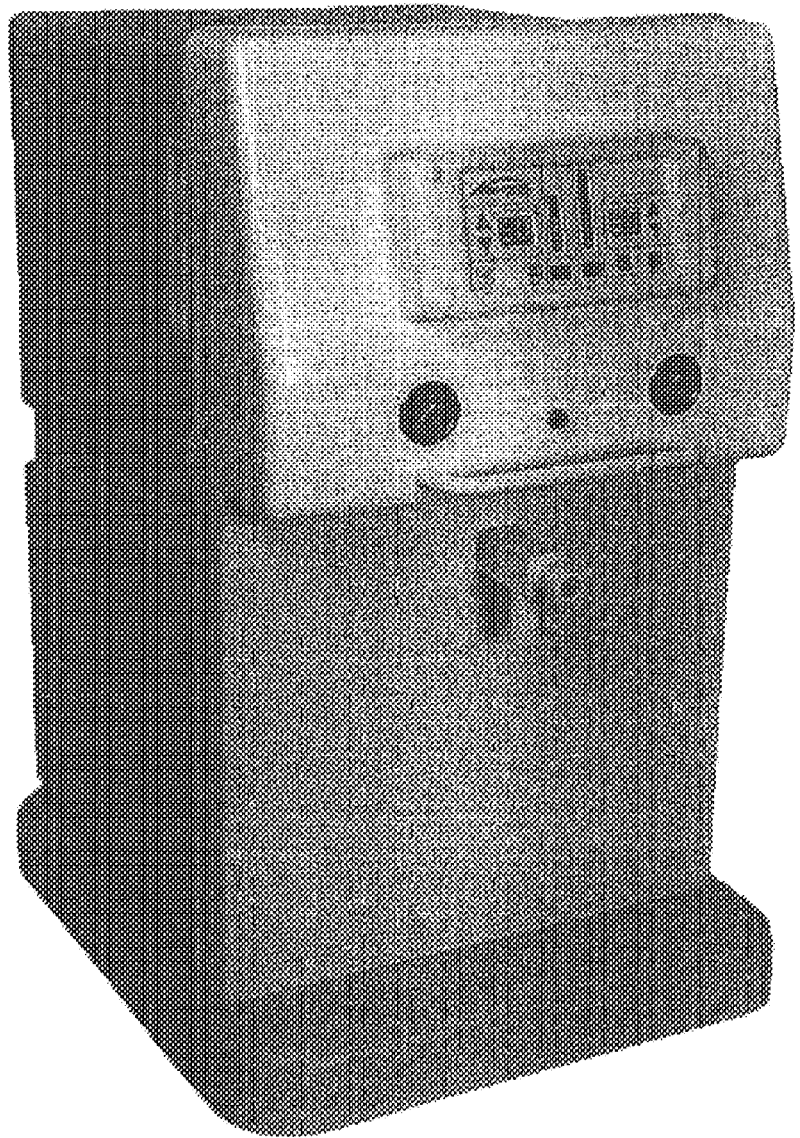
FIG. 9 is a prior art nitrous oxide anesthetic administration system.
Figure 10:
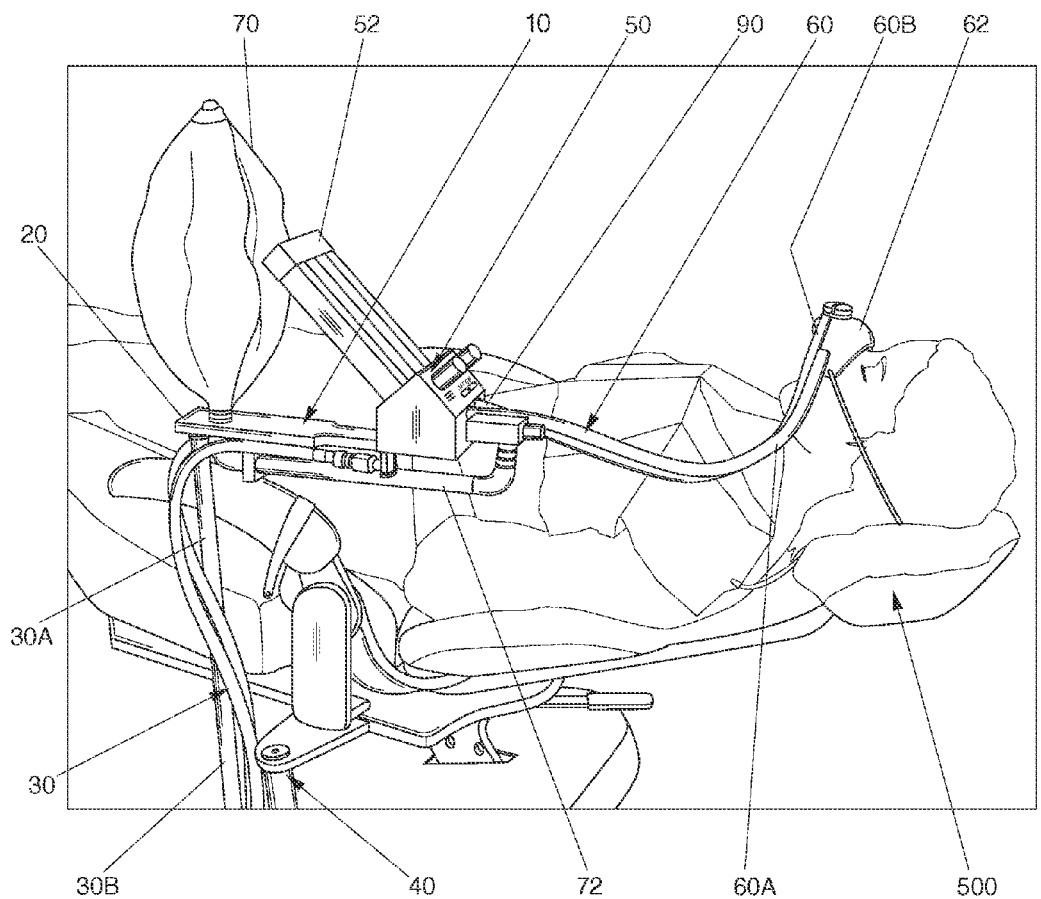
FIG. 10 is a left side view of the nitrous oxide anesthetic administration system of the present invention.
Figure 11:
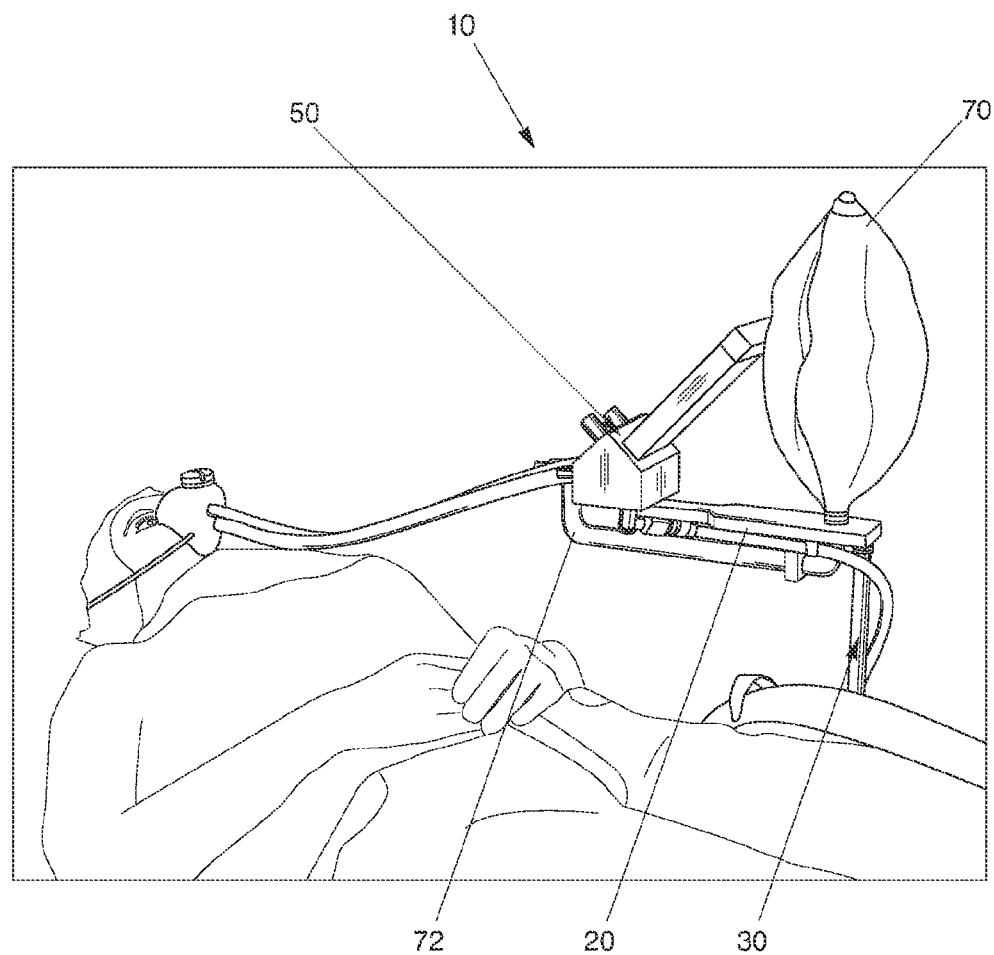
FIG. 11 is a right side view of the invention of FIG. 10.

Referring to FIGS. 10-19, a nitrous oxide anesthetic administration system 10 of the present invention is shown. The present invention is a nitrous oxide administration system 10 which provides convenient, direct access by a medical practitioner, a clear line of vision for the medical practitioner, and flexibility to accommodate the patient and medical professional's needs.

It should be understood that this invention is well suited and preferably used in a dental office environment; however, it may be used in any environment where delivery of objects to a work area is desired. The invention will be disclosed herein in connection with a dental office environment; however, the present invention is not intended to be limited to that particular use and may be used in any health care setting or any setting where a nitrous oxide is required. The configuration of the system components may vary depending on variations in the patient chair, physical site constraints and on the needs of a particular dental practice Most importantly, the nitrous oxide administration system 10 includes a mounting surface structure 20 and adjustable post mechanism 30 which is mounted directly to a patient chair 500 using a mounting plate assembly 40. A system for delivering nitrous oxide is attached to the mounting surface structure 20 or adjustable post mechanism 30 to provide convenient and direct access to the practitioner for delivering the nitrous oxide to the patient, which will be further explained herein.

The nitrous oxide anesthetic administration system may include some elements of prior art nitrous oxide delivery systems. For example, it may include a low-vacuum fluid generated by a vacuum source, a nitrous oxide fluid provided by a nitrous oxide source, and a scavenging mask. In addition, the nitrous oxide safety system may also include an oxygen source, mixing valve, flow meter, breathing bag, and tubing or lines. Note, the nitrous oxide anesthetic administration system of the present invention may also include elements of the system disclosed in "Nitrous Oxide Safety System" (Non-Provisional patent application Ser. No. 12/398,783 filed Mar. 5, 2009).

Referring to FIG. 1, the present invention is a system for administering nitrous oxide 10 which is preferably attached to a patient chair 500. The system generally includes: a mounting surface structure 20, a fluid control system 50 attached to the mounting surface structure 20, a nasal delivery interface system 60 connected to a patient and fluid control system 50, a nitrous oxide and oxygen supply (not shown) fluidly connected to the fluid control system 50, a vacuum source (not shown) for scavenging excess gases, a breather bag 70 fluidly connected to the fluid control system 50 and mounted to the mounting surface structure 20 in a vertical orientation, a mounting plate assembly 40 (FIG. 17) to interface with patient or dental chairs from multiple manufacturers, an adjustable post mechanism 30 attached to the mounting plate assembly 40 and the mounting surface structure 20, supply gas connectors 80A, 80B (FIG. 18) and mixed gas output connector 90 attached to the fluid control system 50, and other hardware, software, lines, and tubing that are necessary to administer nitrous oxide in a health care environment, preferably a dentist's office.

The system includes an adjustable post mechanism 30 attached to a patient or dental chair 500. The adjustable post mechanism 30 may include a cylindrical post 30A that is both pivotally and height adjustable within a corresponding sleeve 30B. The post 30A may slidably engage within the sleeve 30B and may be positioned in a fixed or temporary position when necessary. The post 30A may be secured into a position by use of methods known in the art including ratcheting mechanisms or a tightening collar. The adjustable post mechanism 30 is configured and arranged for height adjustment and pivotal adjustment to provide convenience of use to a practitioner.

Figure 16:
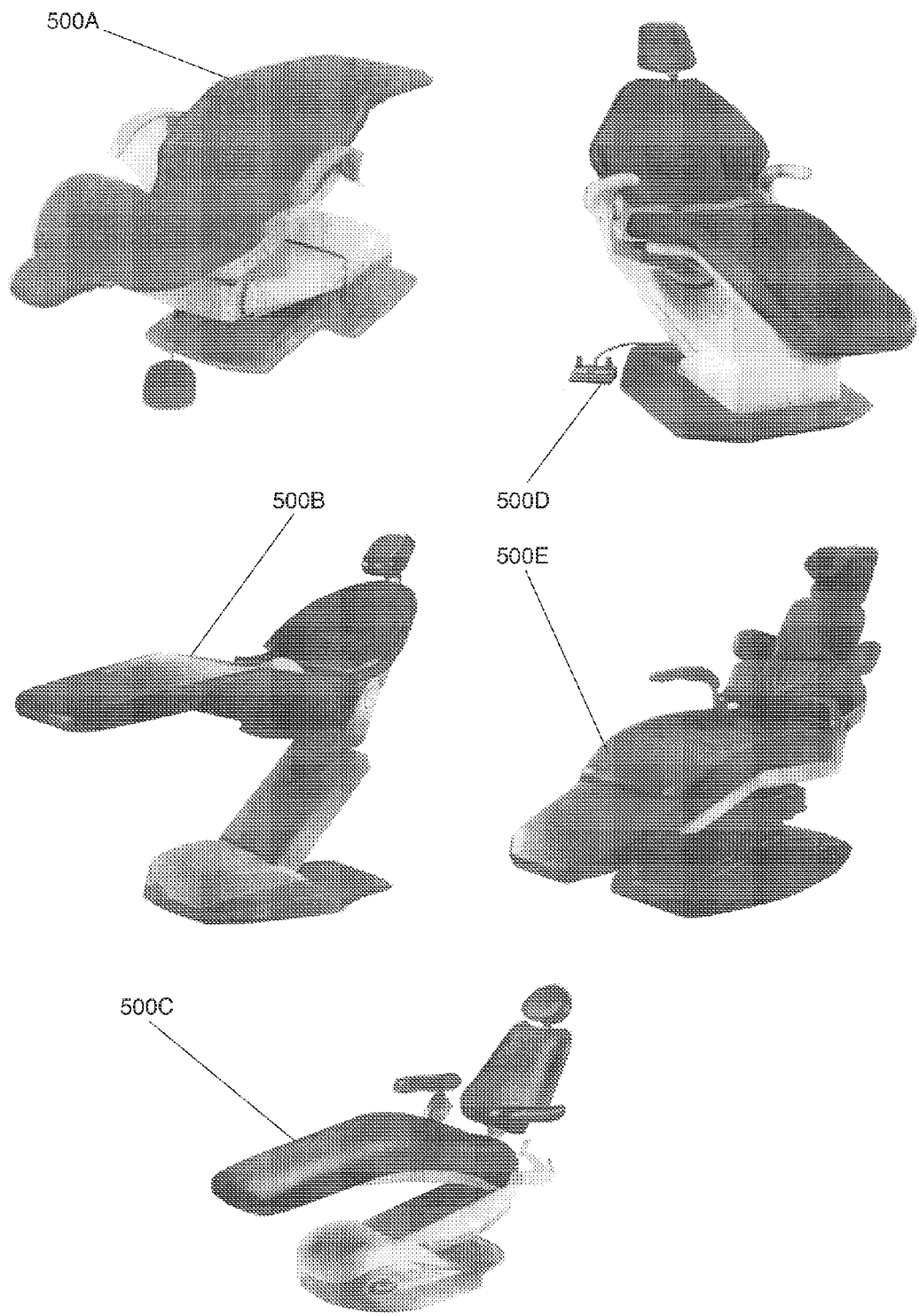
FIG. 16 is a sample of prior art dental chairs which can be utilized with the present invention.
Figure 17:
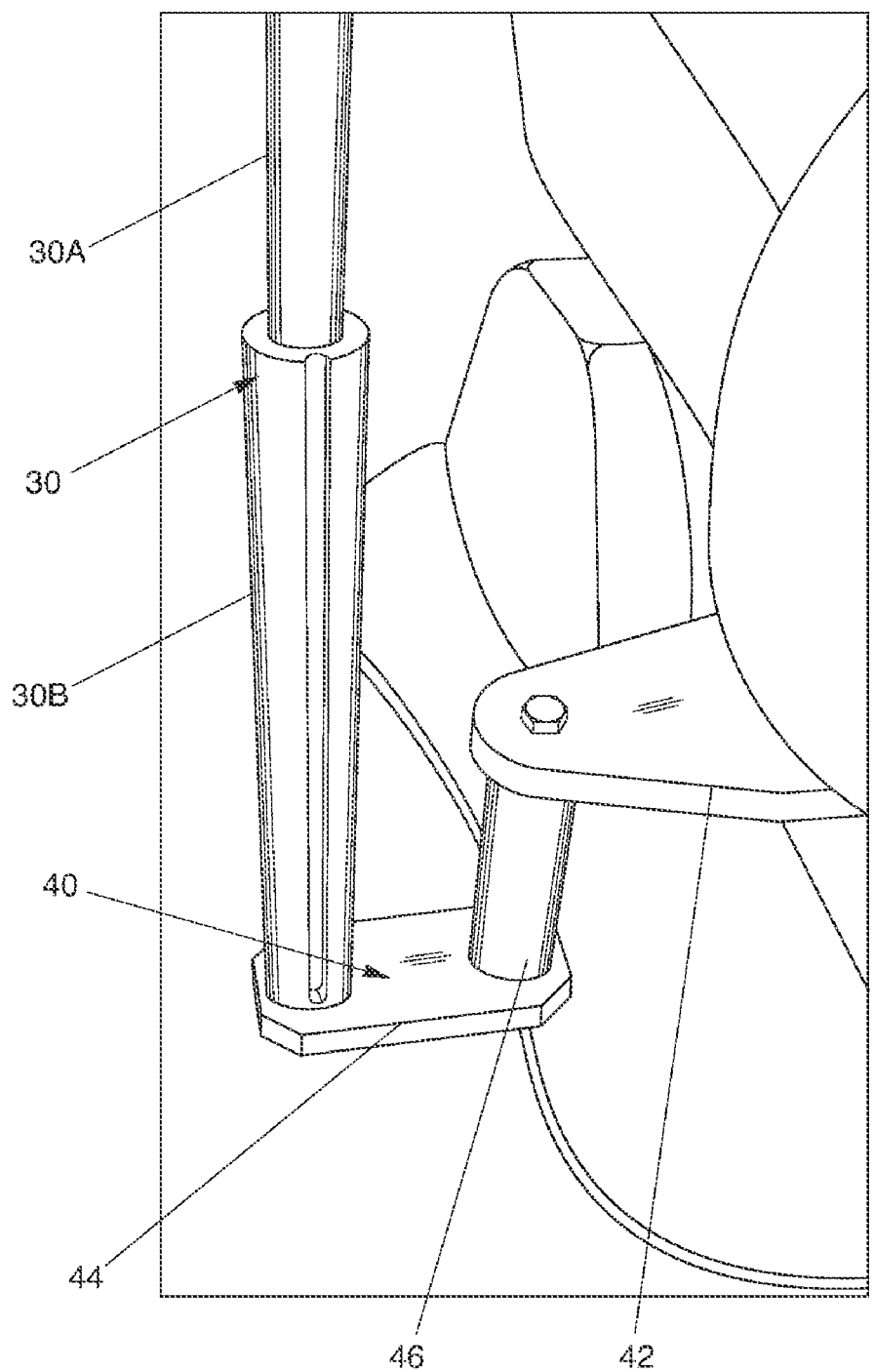
FIG. 17 is a close-up view of a bottom portion of the present invention.

The adjustable post mechanism 30 is attached to a mounting plate assembly 40 which is attached to a lower portion of a patient chair 500. Referring to FIG. 17, the mounting plate assembly 40 may include a chair attachment structure 42, a base plate 44, and a vertical extension structure 46 connecting the chair attachment structure 42 and the base plate 44. The base plate 44 defines an aperture for receipt of a bottom end of the adjustable post mechanism 30. The base plate 44 is attached to the adjustable post mechanism 30 with sufficient strength and can accommodate a wide range of adjustable post mechanisms 30. The base plate 44 lies along a horizontal axis. The chair attachment structure 42 is connected or attached to a bottom or lower portion of a patient chair 500 at a proximal end. The chair attachment structure 42, at the distal end, attaches to an extension structure 46 using methods known in the art. The extension structure 46 attaches to the chair attachment structure 42 and the base plate 44. In one embodiment, the extension structure 46 extends downwardly from the chair attachment structure 42 and is secured, at a top end, to the chair attachment structure 42 using a bolt or other fastener. The base plate 44 then attaches to a bottom end of the extension structure 46. Once the chair attachment structure 42, extension structure 46, and base plate 44 are secured to one another, they form a mounting plate assembly 40 for possible adaptation to other chairs made by various manufacturers. It should be noted that the mounting plate assembly 40 may interface with a variety of patient chairs 500A-E from multiple manufacturers as illustrated in FIG. 16.

The mounting surface structure 20 includes a top surface and a bottom surface. The bottom surface of the mounting surface structure 20 is attached to a top end of the adjustable post mechanism 30. The mounting surface structure 20 is positioned along a horizontal axis or approximately 180 degrees. The mounting surface structure 20 is attached to the breather bag 70 at a proximal end and a fluid control system 50 at a distal end closest to a practitioner.

Figure 14:
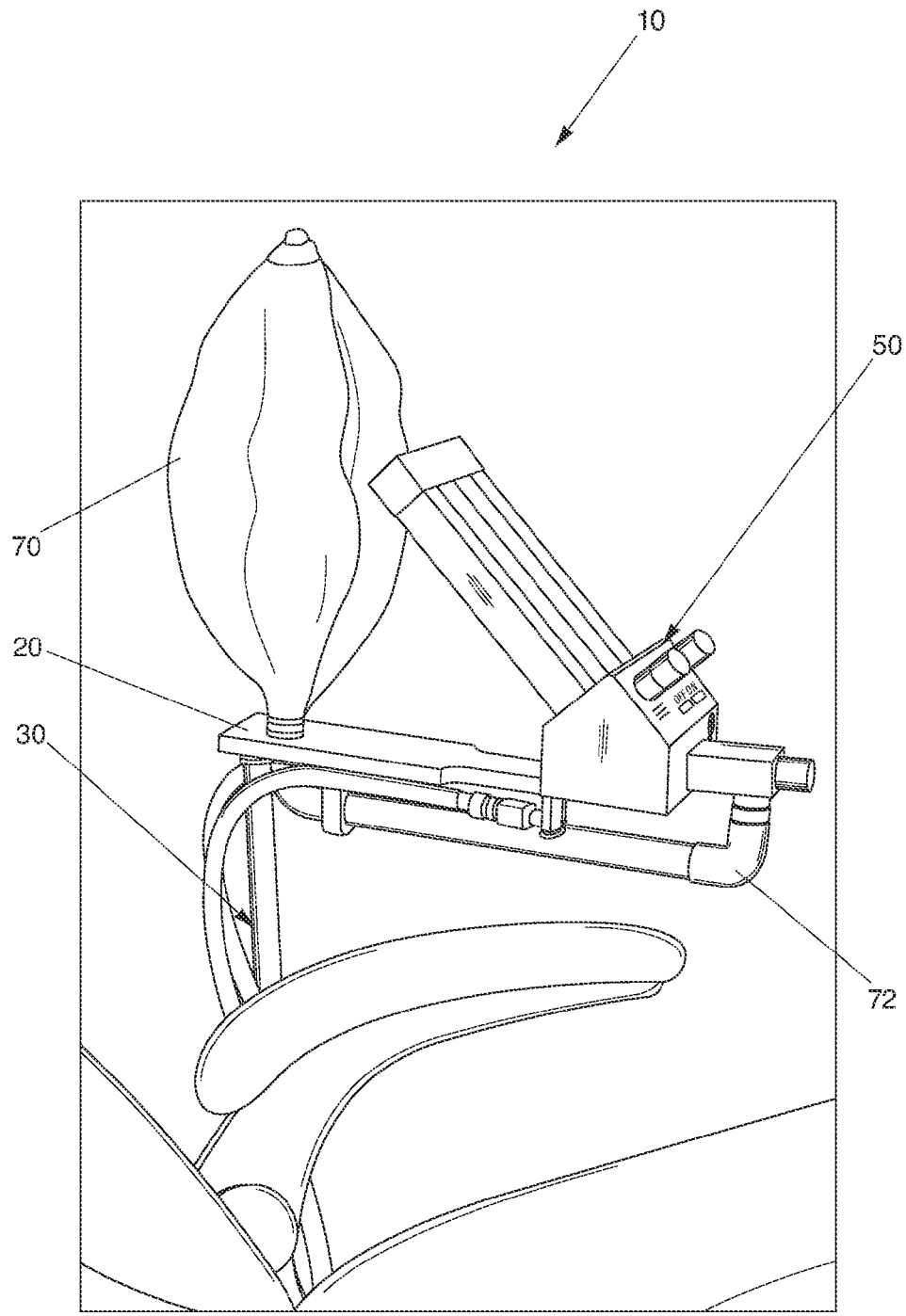
FIG. 14 is a left side view of the invention of FIG. 10.
Figure 18:
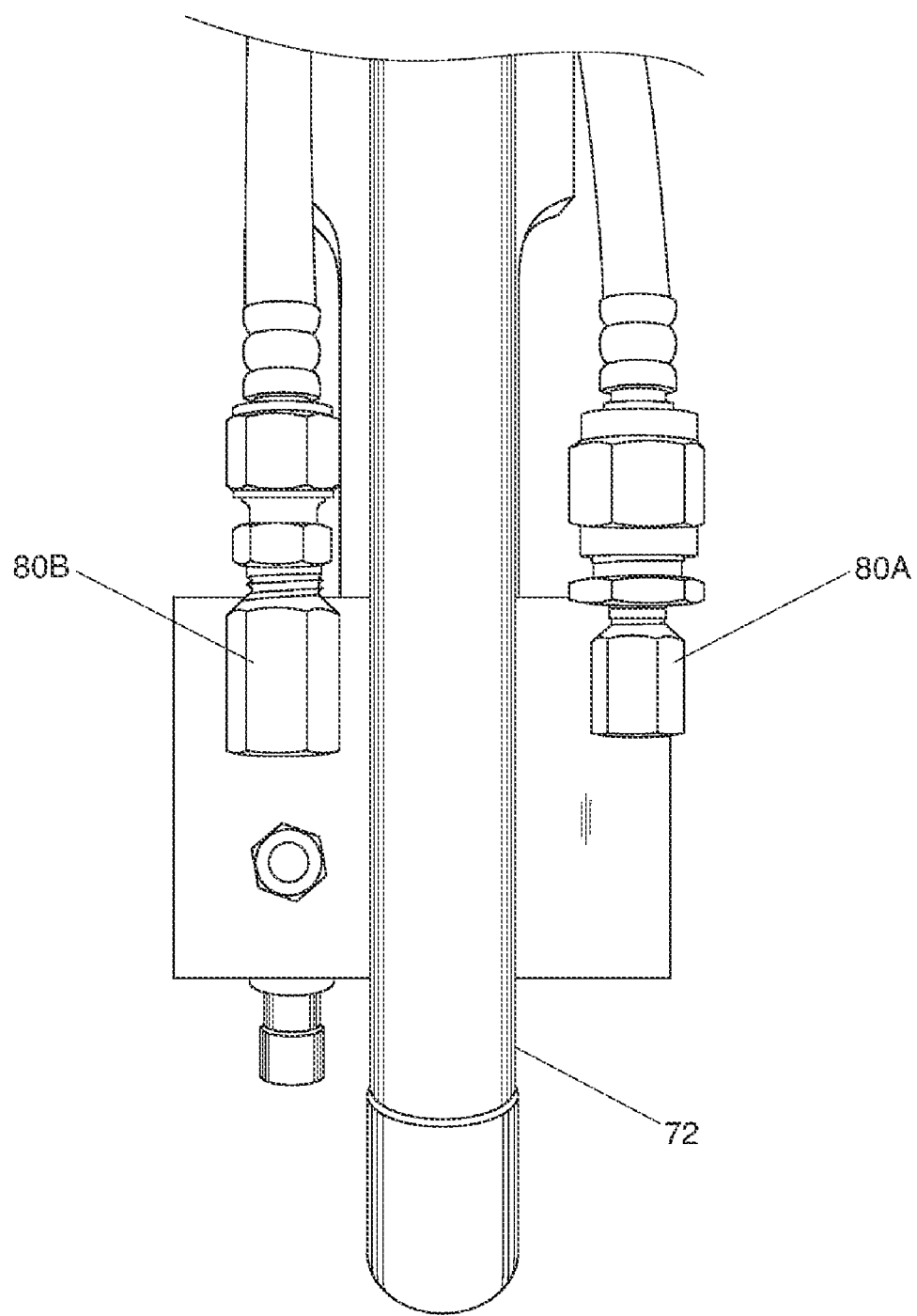
FIG. 18 is close-up view of gas connectors used with the present invention.
Figure 19:
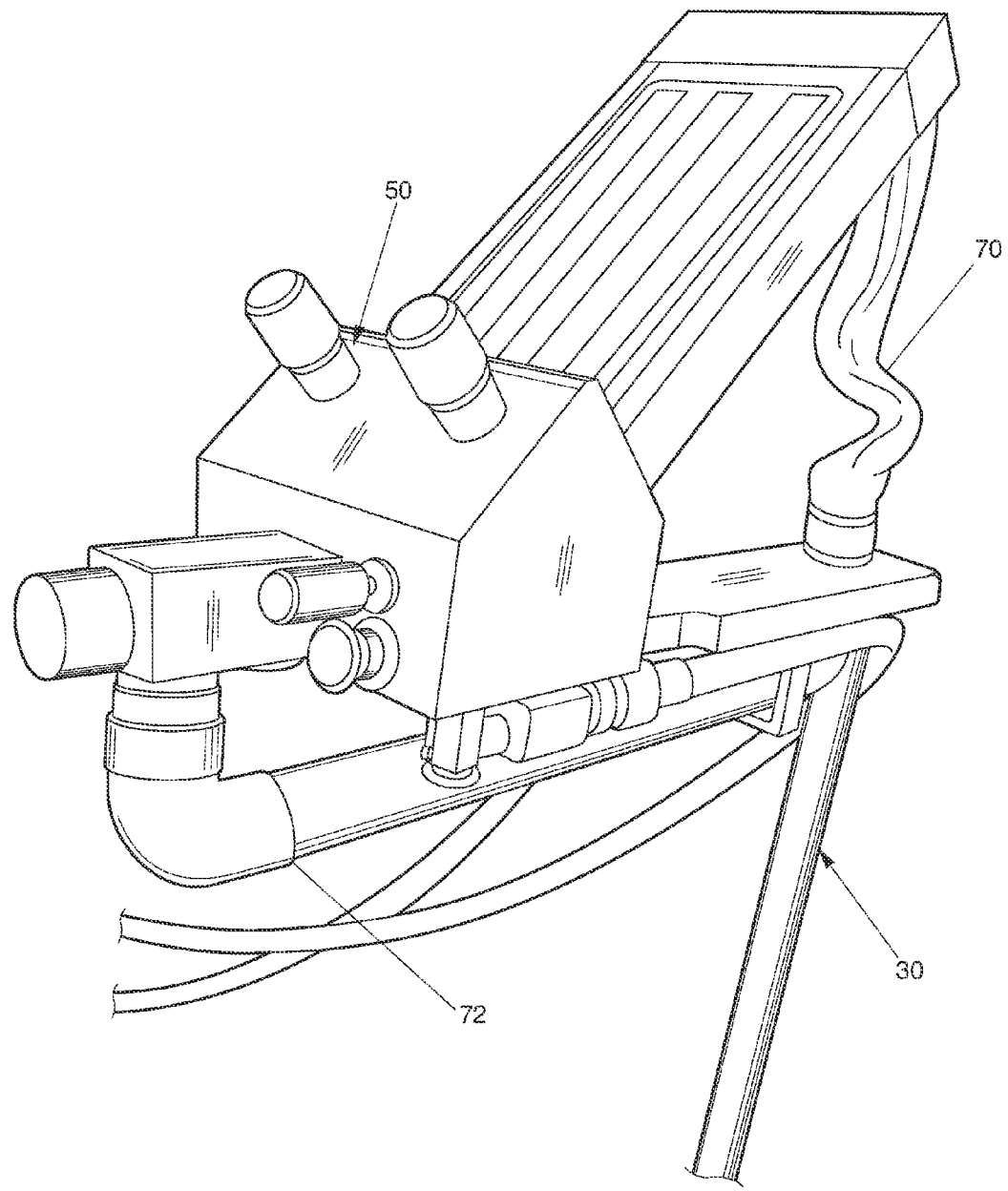
FIG. 19 is a front perspective view of the present invention.

Referring to FIGS. 14 and 19, a fluid control system 50 for controlling the flow of nitrous oxide and oxygen is attached to the mounting surface structure 20. The fluid control system 50 includes a fluid flow meter 52 mounted on a top surface of the fluid control system 50. A display of the fluid flow meter 52 is positioned along a vertical axis at less than 90 degrees, preferably between 30 degrees to 45 degrees, relative to the mounting surface structure 20 to provide a better view to the practitioner. Referring to FIG. 18, the nitrous oxide and oxygen supply (not shown) is fluidly connected to the fluid control system 20 using fluid connectors 80A, 80B fixedly attached to the bottom surface of said mounting surface structure 20. The fluid control system 50 also includes an emergency air intake port.

Figure 12:
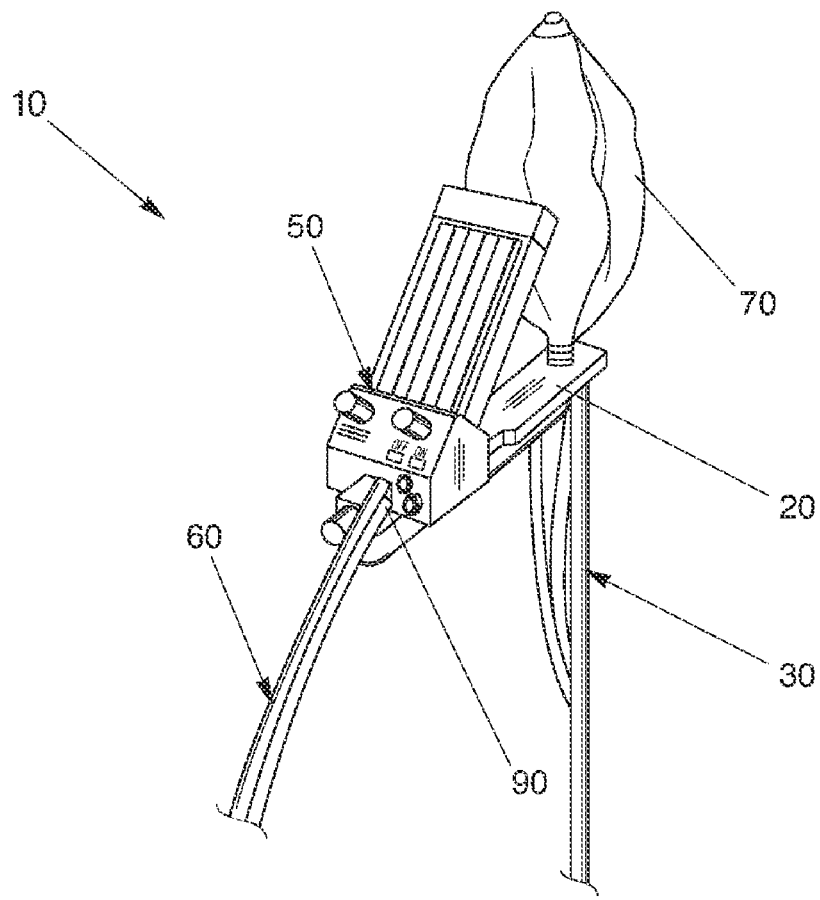
FIG. 12 is front perspective view of the invention of FIG. 10.
Figure 13:
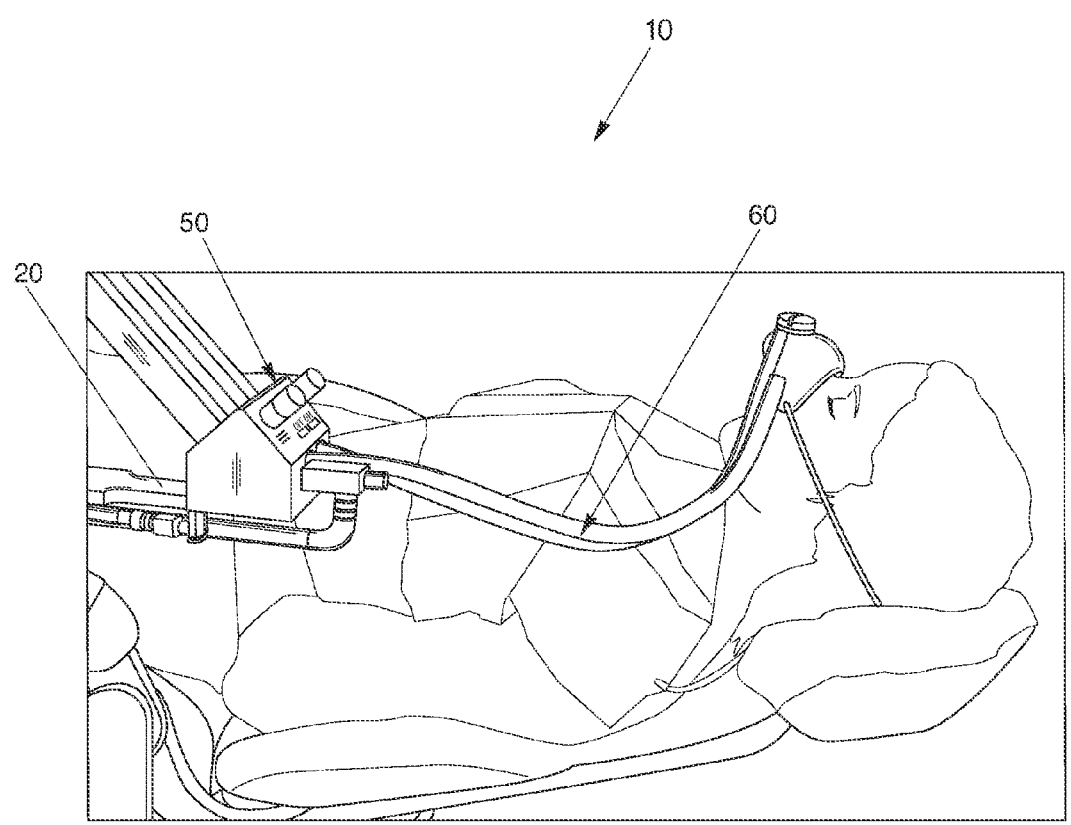
FIG. 13 is a partial left side view of the invention of FIG. 10.

Referring to FIGS. 12-13, a nasal delivery interface system 60 is fluidly connected to the fluid control system 50. The nasal delivery interface system 60 includes a single scavenging tube 60B and a single nitrous oxide and oxygen tube 60A fluidly connected to a single nasal delivery mask 62. The fluid control system 500 including a mixed gas output connector 90 fluidly connected to the single nitrous oxide and oxygen tube 60A. A vacuum source (not shown) is fluidly connected to the single scavenging tube 60B for scavenging excess gases and the fluid control system 50. Note, the vacuum source may be provided by a variety of methods known in the art.

Figure 15:
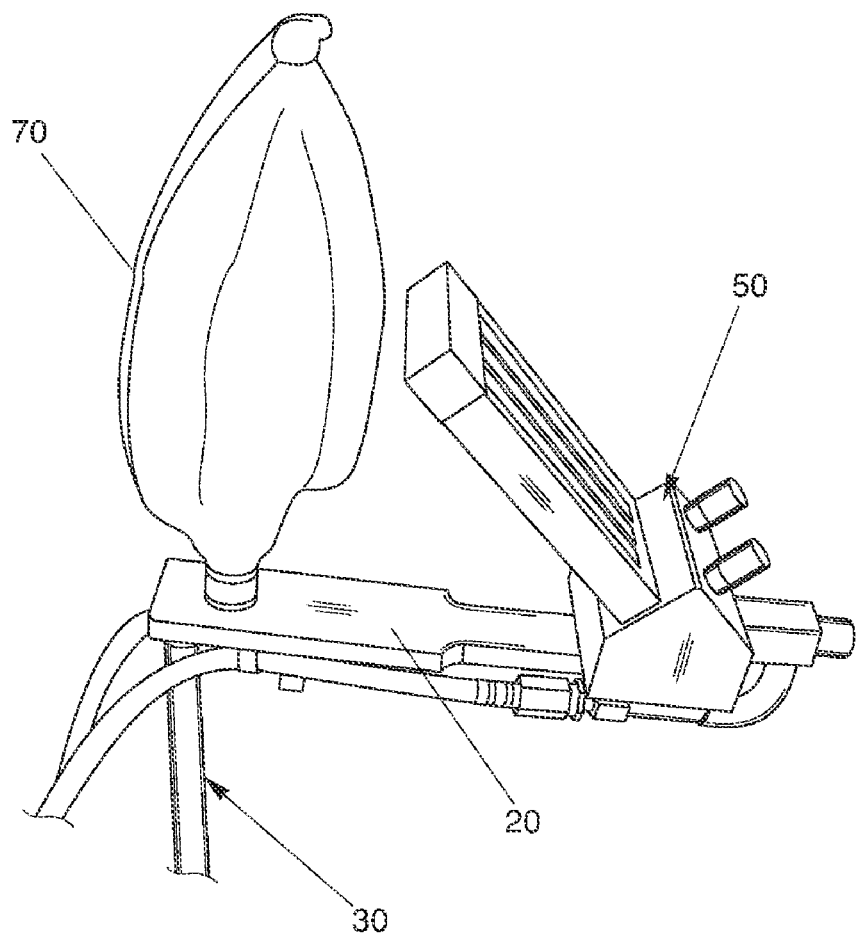
FIG. 15 is a rear perspective view of the invention of FIG. 10.

Referring to FIG. 15, the breather bag 70 is vertically mounted to a top surface of the mounting surface structure 20. The breather bag 70 is positioned along a vertical axis or about 90 degrees depending upwardly from the mounting surface structure 20. The breather bag 70 is mounted rearward or behind the fluid control system 50 to allow full view of fluid flow meter display 52. The breather bag 70 is fluidly connected to the control system 50 by way of an elongated tubular structure 72 attached to a front surface of the fluid flow meter 52.

In operation, the present invention provides a system for administering anesthesia/analgesia gas 10 or any type of gases which provides convenient and direct access to a medical practitioner. The practitioner connects the nasal delivery interface system 60 to the patient and to the fluid control system 50. After the nasal mask 62 is attached to the patient, the nitrous oxide/oxygen gas, or anesthetic, is turned on and the gas enters a single tube 60A fluidly connected with the nasal delivery mask 62. Throughout the administration of the gas, the system 10 allows the practitioner a direct view and a close proximity to the upright breathing bag 70, fluid control system 50 including display 52, patient, and all other parts of the nitrous oxide administration system 10 which makes the administration of the gas much more efficient, safe, and less time consuming. Also, the mounting of the nitrous oxide anesthetic administration system 10 to a patient's chair provides greater stability and convenience to a practitioner.

In summary, the present invention provides a system for administering anesthesia/analgesia gas 10 which provides convenient, direct access by a medical practitioner, a clear line of vision for the medical practitioner, and flexibility to accommodate the patient and medical professional's needs. The present invention is a novel configuration which mounts the control system, monitoring devices, safety devices and breather bag which mounts directly or indirectly to the patient chair.

Some of the benefits of the proposed novel invention are as follows. The present invention shortens hoses from the fluid control system to the patient to reduce cost, complexity and weight. The present invention minimizes control input to nasal delivery interface device output (latency) by at least 50% by shortening hose length. The present invention minimizes patient head access limitation and movement restriction by minimizing hose lengths, stiffness and multiples. The present invention eliminates dual hoses for each of: O2/N2O and scavenge. The present invention puts controls within direct, forward reach of doctor (from normal treatment position) throughout procedure. The preset invention puts displays and gauges in direct view of doctor and assistant throughout procedure to enhance practitioner and patient safety. The present invention provides open passage around patient and patient support chair by eliminating support cart. The present invention provides open passage around patient and patient support chair by eliminating tubing crossing passageways. The present invention eliminates potential of toppling cart and damaging systems by eliminating tubing crossing passageways. The present invention eliminates the potential danger caused by damaging a high pressure gas system. The present invention maximizes visibility of breather bag by doctor and assistant throughout procedure by orienting breather bag, or bellows, superior to inlet rather than current designs which hang breather bags inferior to their inlet. The present invention reduces patient anxiety prior to their procedure by reducing the visual impact of the anesthetic apparatus. The present invention minimizes system size, complexity and cost. The present invention has system configuration adaptable to all operatory configurations. The present invention has a system capable of mounting to most commercially available patient chairs via model specific interface plates. Most importantly, the present invention mounts directly to the patient chair to accomplish all of the above.

Therefore, while there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A system for administering nitrous oxide comprising:
   an adjustable post mechanism attached to a mounting plate assembly which is attached to a lower portion of a patient chair, said adjustable post mechanism configured for height adjustment and pivotal adjustment;
   a mounting surface structure having a top surface and a bottom surface, said bottom surface of said mounting surface structure attached to the adjustable post mechanism, said mounting surface structure positioned along a horizontal axis;
   a fluid control system for controlling the flow of nitrous oxide and oxygen attached to the mounting surface structure, said fluid control system including a fluid meter display mounted on a top surface of said fluid control system, said fluid meter display positioned along a vertical axis at less than 90 degrees relative to the mounting surface structure;
   a nasal delivery interface system fluidly connected to the fluid control system, said nasal delivery interface system including a single scavenging tube and a single nitrous oxide and oxygen tube fluidly connected to a nasal delivery mask;
   said fluid control system including a mixed gas output connector fluidly connected to said single nitrous oxide and oxygen tube;
   a nitrous oxide and oxygen supply fluidly connected to the control system using fluid connectors fixedly attached to bottom surface of said mounting surface structure;
   a vacuum source fluidly connected to the scavenging tube for scavenging excess gases; and
   a breather bag mounted to a top surface of the mounting surface structure, said breather bag positioned along a vertical axis about 90 degrees depending upwardly from the mounting surface structure, said breather bag attached rearward of said fluid control system to allow full view of fluid meter display, said breather bag fluidly connected to the control system using an elongated tubular structure.

2. A system for administering nitrous oxide comprising:

an adjustable post mechanism attached to a mounting plate assembly which attached to a lower portion of a patient chair, said adjustable post mechanism configured for both height adjustment and pivotal adjustment;

a mounting surface structure having a top surface and a bottom surface, said bottom surface of said mounting surface structure attached to the adjustable post mechanism;

a fluid control system for controlling the flow of nitrous oxide and oxygen attached to the mounting surface structure;

a nasal delivery interface system fluidly connected to the fluid control system;

a nitrous oxide and oxygen supply fluidly connected to the control system;

a vacuum source fluidly connected to the nasal delivery interface system; and a breather bag vertically mounted to a top surface of the mounting surface structure, said breather bag positioned along a vertical axis depending upwardly from the mounting surface structure, said breather bag fluidly connected to the control system using an elongated tubular structure.

3. A system for administering nitrous oxide comprising:

an adjustable post mechanism attached to a dental chair, the adjustable post mechanism including a cylindrical post configured for pivotal and height adjustment within a corresponding sleeve along a vertical axis;

a mounting plate assembly connected to a lower portion of the dental chair and to a bottom end of the adjustable post mechanism, the mounting plate assembly includes a chair attachment structure connected to a base plate which are both positioned along a horizontal axis, the base plate defines an aperture for receipt of the bottom end of the adjustable post mechanism;

a mounting surface structure having a top surface and a bottom surface, said bottom surface of said mounting surface structure attached to a top end of the adjustable post mechanism; and a means for administering nitrous oxide attached connected to the mounting surface structure or adjustable post mechanism.

* * * * *